United States Patent

Applegate

[11] 4,127,120
[45] Nov. 28, 1978

[54] TORSO-BOARD STRAPS AND METHOD OF USING THE SAME

[76] Inventor: Lee C. Applegate, 7645 Sumter Hwy., Apt. 101E, Columbia, S.C. 29209

[21] Appl. No.: 739,616
[22] Filed: Nov. 8, 1976
[51] Int. Cl.$^2$ .............................................. A61G 1/00
[52] U.S. Cl. .................................... 128/134; 5/82 R; 128/DIG. 15; 269/328
[58] Field of Search ............... 128/134, 133, DIG. 15, 128/87 R, 87 C; 5/82 R; 2/44, 45, DIG. 6; 224/6; 269/328, 322

[56] References Cited

U.S. PATENT DOCUMENTS

| | | | |
|---|---|---|---|
| 3,535,719 | 10/1970 | Murcott | 128/134 X |
| 3,707,734 | 1/1973 | Matthews | 5/82 |
| 3,757,359 | 9/1973 | Stellman | 5/82 X |
| 3,889,668 | 6/1975 | Ochs et al. | 128/134 |

Primary Examiner—Robert W. Michell
Assistant Examiner—Michael H. Thaler
Attorney, Agent, or Firm—Eugene F. Friedman

[57] ABSTRACT

A pair of straps used in retaining on a torso-board a person with neck or back injuries. General use requires two sets of these straps to adequately restrain the patient. The two straps in a set attach to opposite corners of the board, utilizing openings through it at those locations. The free ends of the straps then connect to each other to secure the injured person. The attachments of the straps to the board allow changes in the overall effective lengths of the straps. Sections of loops and hooks on the straps achieve these variable attachments to the board. The straps' free ends may also connect together at different positions to produce the required tension to immobilize the individual. One of the straps' free end may include a metal loop with the other possessing sections of engageable hooks and loops. Passing the latter partially through the metal loop and engaging hooks with loops connects the two straps together. The straps' attachments to the board and their variable connection permit the necessary adjustments to accomodate the particular position of the injured person on the board and to remove any possible slack that may occur during their use. The straps need not pass across the back of the board; consequently, the subsequent relocation of the restrained person upon a full length board may proceed with a minimum of deleterious jostling.

13 Claims, 8 Drawing Figures

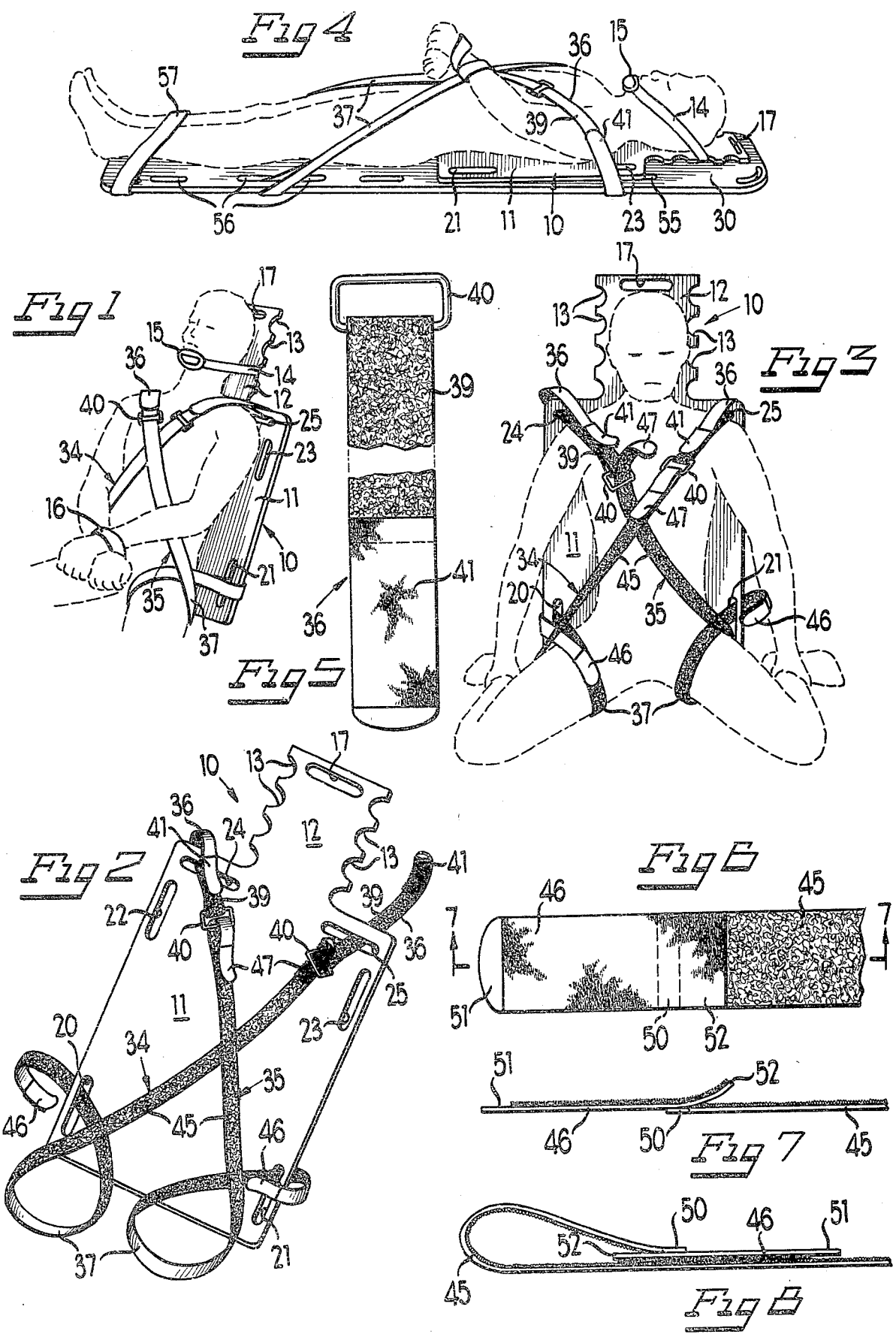

TORSO-BOARD STRAPS AND METHOD OF USING THE SAME

BACKGROUND

A person suffering injuries to his back or neck generally requires some degree of immobilization until he receives full medical attention at a hospital. Depending upon the location of the accident and any resulting debris, the individual may require two stages of such immobilization. The first stage precludes motion during the extrication from his immediate predicament as often occurs in the case of automobile accidents.

The second immobilization places the patient in a condition suitable for transportation to a medical facility. In this position, the patient lies immobile upon a flat, rigid, stiff structure running the entire length of his body.

The structure employed in first immobilizing stage, however, involves a board extending only from the patient's head down to the region of his hips. Known as a torso-board, it generally includes openings to accomodate straps which will secure the patient to the board with his knees bent towards his chest.

Such a board appears generally at 10 in FIGS. 1 through 3 of the drawings and includes the large rectangular area 11 which supports an injured person's back. The smaller region 12, integral with one side of the large area 11, performs a similar function for a person's neck by immobilizing his head. The small section 12 includes the semicircular cutouts 13 along both sides. As shown in FIG. 1, the strap 14 fits inside a cutout 13 on either side of the section 12. Tightening the cup 15 onto the individual's chin keeps the head against the board's section 12 and prevents motion.

The auxiliary strap 16 holds the patient's wrists together. Moreover, the small area 12 also includes the opening 17 at its top to facilitate carrying the board either with or without a patient on it.

The board's large area 11 includes the openings 20 and 21 at its bottom coinciding with the patient's pelvic or hip area. Further, a pair of lateral openings 22 and 23 appear in the region around the patient's shoulders. Lastly, the openings 24 and 25 occur at the top of the larger portion 11 and generally fall slightly above the patient's shoulder. The two shoulder openings 22 and 24 on one side and the openings 23 and 25 on the other side permit different orientations of the staps to the patients they retain. These accomodate differences in the heights and sizes of the patients as well as the types of injury incurred. The latter openings 22 and 23 also facilitate a patient's subsequent placement on a full-length board as discussed below.

Many emergency medical units currently possess torso boards similar to that shown at 10. They may have purchased these, or even fashioned them out of sheets of plywood.

The use of these boards, however, requires some form of straps to retain the patient in an immobilized condition. Previously, straps similar in construction to safety belts for automobiles and airplanes performed the function. Specifically, they assumed the form of nine-foot long straps with a metal buckle at one end and a metal tongue near the other end. In operation, the technician extended the belt across the back of the board; passed its ends through openings at opposite corners; and latched together the tongue and buckle with the lower portion of the strap wrapped around the leg to immobilize the pelvic region. Two belts utilized in this fashion normally provided sufficient restraint.

The use of the straps, however, suffers from several shortcomings. First its application may represent a difficult, inconvenient, and perhaps injurious task. Applying the straps requires access to the back of the board. The patient's predicament may prevent the application of the straps before the placement of the board adjacent to the patient. Consequently, the proper threading of the straps through the holes and around the back may produce substantial movement of both the board and the patient. This motion can seriously and deleteriously affect the patient's condition.

Furthermore, this type of strap admits of only one type of adjustment. Specifically, the overall length may undergo alteration. However, this can only occur by separating the buckling, moving the metal tongue to a different position on the strap, and rebuckling the strap. Upon its unbuckling, though, all immobilizing tension from the strap disappears; the two free ends cannot restrain the patient whatsoever. Furthermore, the adjustment may not proceed facilely, since part of the strap wraps around the patient's leg and a further part goes behind the board; the slack may not readily disappear.

Moreover, the buckle used to hold the strap together itself involves substantial bulk and weight. It can bounce against the chest or, during the patient's handling, press against him, producing bruises and further injuries.

Moreover, extricating the patient from his situation requires moving him and the board both relative to the earth. The process may also effect a shift in the patient's weight relative to the board and the straps. This can result in the straps becoming loose and not providing the requisite immobility. Tightening them involves moving the board back and forth to remove slack in the back again as well as attempting to change the strap position around the legs. Once again, moreover, the ends of the strap may have to unbuckle from each other to allow adjustment of their effective length.

Subsequent to his removal from his immediate predicament, the patient should normally assume a completely flat position on a full-length board as in FIG. 4. The previous straps, however, interfere with the torso board 10 lying flat and motionless upon the full-length board 30. Consequently, placing the patient upon the latter requires the complete disengagement of the straps from the patient while on the torso board 10. Further deleterious motion results as the torso board and the patient are then placed on the long board 30 or the patient alone shifted to it.

Lastly, placing the patient on the full-length board 30 requires unfastening the straps from his legs so that they may lay flat. Releasing the buckles that hold the straps together, however, simply permits the legs to drop from their bent position. This drastic motion, unless very carefully guarded against, will considerably shock the system and aggravate the injuries. Preventing this undesired motion requires two medical personnel; one must control the motion of the legs while the other unbuckles the straps.

SUMMARY

Attaching the straps to the torso board at openings near its corners eliminates extending the straps across the board and back. Consequently, applying the straps with the patient on the board does not require manipulating the board to gain access to its rear. As a result, the use of the board becomes facilitated and produces less motion and consequent injury to the patient.

Attaching the strap to the corners while permitting adjustment across the chest requires a set of two straps in place of the previous single strap. The first strap in the set includes a first attaching means for adhering one end to the board at an opening near the shoulders. The second strap has a second attaching means for adhering of its one ends at a second opening on the board's other side and near the patient's hips. The straps' other or free ends then include a two-portion connecting means, one portion forming part of each strap, for joining them together to restrain the patient. Two sets, each with two straps, will suffice to immobilize the patient upon the board.

Generally, a set of straps, of course, allows adjustment at its middle through the connecting device. This adjustment can achieve the general overall tightness required to restrain the patient.

Additionally, the second strap may also permit adjustments where it attaches to the opening at the bottom of the board. This has particular importance since this portion of the strap wraps around the leg to retain it in a bent attitude toward the patient's torso. This adjustment removes the slack in the strap around the leg by tightening the attachment of this strap to the board.

A further adjustment may occur in the first attaching means which adheres the upper strap to the board near an upper opening. This adjustment may prove useful in removing slack occurring near the shoulders.

Providing sections of engageable loops and hooks on the straps, such as that sold under the Velcro trademark, accomplishes the desired adjustability. It also allows a wide latitude of choices in the configurations of the straps to permit the secure and firm immobilization of the patient. Moreover, these components do not rust, clog or present a danger of injury to the patient.

Specifically, the end of the strap may, for example, have a section of hooks. A major portion of the rest of the strap may have loops that engage the hooks. Placing the hooks through the opening and holding it back upon the strap allows the hooks to engage the loops. Since the hooks may engage the loops at almost any desired or needed location, the straps may attach to the board with a vast multitude of different effective lengths.

The hooks and loops may also provide similar advantages to the connecting device that holds together the free ends of the straps. Specifically, the free end of the shoulder strap may have a metal loop connected to it. The lower strap's end may have a section of hooks which in turn adjoins an extended section of loops. The section of hooks passes through the metal loop, folds back upon the strap and engages the loops. The hooks may again connect to the loops at any of an infinite number of locations; the choice results simply from placing the one in contact with the other at the desired spot.

Lifting the hooks off the loops effects their disengagement. Moreover, this disengagement does not necessitate releasing the tension between the two straps in the set. Lifting up the sections of hooks while maintaining a firm grasp prevents that end of the strap from slipping through the metal loop. The tension between the straps may be increased or decreased by slowly moving the section of hooks away from or toward the metal loops on the other strap. In particular, this method permits the gentle and gradual change in position from that on a torso board with the legs bent to the flat position on a full-length board.

To strap a patient to a torso board first involves placing the board in the proper position relative to the injured person. One end of each of the two upper straps then passes through the shoulder openings in the board and folds back upon itself to attach to the board. Similarly, the end of each of the two lower straps passes through the hip openings and connects itself to similarly attach those straps. The lower straps may then wrap around the legs and connect to the upper straps. Any needed adjustments in the tension may occur where the straps connect together or where they attach to the board.

BRIEF DESCRIPTION OF THE FIGURES

FIG. 1 gives a perspective view of a torso board holding a patient immobilized upon it with two sets of torso straps.

FIG. 2 has a perspective view of the board and straps with some of the straps unfastened.

FIG. 3 gives a frontal elevational view of the torso board of FIGS. 1 and 2 with the patient occupying a somewhat different position then in FIG. 1.

FIG. 4 provides a side elevational view of a patient in contact both with a torso board and a full-length board but whose position has changed from the bent-leg position of the former to the flat position suitable for transportion.

FIG. 5 shows the construction of the shoulder strap used with the torso board.

FIG. 6 depicts one end of the lower strap.

FIG. 7 gives a cross-sectional view along with the line 7—7 of the end of the lower strap of FIG. 6.

FIG. 8 has a side view of the end of the lower strap with the hooks engaging the loops and showing the connection between the two sections which avoids their disengagement under the usually encountered stresses.

DETAILED DESCRIPTION

Restraining a patient to the torso board 10 requires in general the two sets of straps 34 and 35. As shown in FIG. 2, each set 34 and 35 includes a first or shoulder strap 36 and a lower or second strap 37.

The shoulder strap 36, seen more clearly in FIG. 5, includes a section of loops 39 which extends most of its length. At one end, it includes the metal loop 40, and at the other end appears a short section of hooks 41 engageable with the loops 39.

Returning to FIG. 2, to attach the shoulder strap 36, the hooks 41 pass through the upper shoulder openings 24 or 25 as shown, or, alternatively, through the lateral shoulder openings 22 or 23. The hook section 41 then folds back around the edge of the board 10 to engage the loops 39 with the hooks 41 engaged to the loops 39, the shoulder strap 36 remains attached to the board 10.

The lower strap 37 also includes a section of loops 45 which extends most of its length. At both ends of the lower straps 37, however, appear short sections of hooks, 46 at one end and 47 at the other. Both ends of the strap 37 have the construction as shown in FIGS. 6 and 7 which, for convenience, shows only the section of hooks 46. The section of loops 45 connects to the section of hooks 46 in an area 50 intermediate the ends 51 and 52 of the hooks section 46. Both ends 51 and 52 of the section of hooks remain free to move away from and out of contact with the section of loops 45. Consequently, as shown in FIG. 8, any force tending to disengage the hooks 46 from the loops 45 is exerted upon the interior region 50 of the hooks 46. The loops and hooks, however, resist pressures exerted upon the interior of the adjoined sections. Thus, although the force, if exerted upon the end 52 of the hooks 46 could disengage the two sections, when applied to the interior 50 of the hooks 46, does not pull them apart.

The lower straps 37, of course, attach to the board 10 in a fashion very similar to the upper or shoulder straps 36. Specifically, the section of hooks 46 passes through the opening 21 and folds back and engages with the loops 45 at a point producing the desired effective length to the strap 37.

After its attachment to the board 10, the strap 37 then typically passes around the leg; it first proceeds over the top, around the inner surface, across the back and around the outside. The remaining end 47 of the strap 37 travels across the patient's torso toward the shoulder strap 36 on the other side of the patient as suggested in FIGS. 1, 2 and 3. The section of hooks 47 then passes through the metal loop 40 of the shoulder strap 36. The technician then pulls the section of hooks 47 back toward the hip opening 20 or 21, from where the strap 37 came, to achieve the requisite tension. Engaging the hooks on the section 47 with the loops 45 completes the application of the set of straps 34 or 35 to the patient. The technician may then proceed to apply the second set in the same fashion to produce the results shown in FIG. 1.

To remove slack developed while applying the second strap set, the first set may require further adjustment. Furthermore, moving the patient may cause a change in his position which can also develop slack in one or both of the straps. The set of straps 34 and 35 each possess three modes of adjustment should such a problem develop. FIG. 3 illustrates these possibilities for the strap set 35.

For looseness near the patient's right shoulder, the technician may disengage the section of hooks 41 from the shoulder strap 36. Pulling it toward the patient's left leg and reengaging it with the loops 39 closer to the metal buckle 40 effectuates the desired tightening. For general overall looseness, or even that near the shoulder discussed above, the technician can peel the hooks 47 from the loops 45 on the lower strap 37. He may then pull the hooks section 47 further toward the patient's left leg to increase the tension along that strap. When sufficiently tight, he may reengage the hooks 47 with the loops 45 to retain them in place.

The hooks 46 at the other end of the strap 37 provides an especially important adjustment for a patient on the torso board. As discussed above and shown in FIG. 3, the strap 37 wraps around the patient's leg. Looseness near the end of the strap where it passes through the opening 21 does not readily disappear through an adjustment at the metal loop 40. Doing so would require manipulating the strap 37 around the leg in the hope that the excess material could be brought to where pulling on the end 47 would provide the necessary tautness. With the straps shown, such manipulation becomes unnecessary. Instead, the technician may simply peel off the hooks 46. He then pulls the hook section 46 in a direction to pass more of the strap 37 through the opening 21 and thus remove the slack. Reengaging the hooks 46 with the loops 45 effectuates the tightening around the leg.

The patient's injuries may dictate that he assume a completely flat position for transportation to a hospital. The straps 34 and 35 not only retain the patient to the torso board, they also immobilize him in a flat position upon a full-length board 30, illustrated in FIG. 4. To achieve the supine position, the technician first peels off a section of hooks 47 from either of the strap sets 34 or 35; however, he retains a secure hold of the hooks section 46 against the metal loop 40 to prevent precipitous motion of the leg that could induce further injuries. He then slowly allows the lower strap to pass through the metal loop 40 until the leg lies flat. The second set of straps then receives the same treatment. With the patient lying flat upon the board 30, the technician disengages the hooks 41 from the loops 39 on the shoulder straps 36. He slips them out of the upper torso board openings 24, into the lateral openings 23 on the torso board, and through the side openings 55 on the full-length board 30. Reengaging the hooks 41 to the loops 39 affixes the strap 36 and the torso board 10 to the long board 30. Further the technician simply removes the lower strap 37 from the openings 21 of the torso board 10 and engages them with one of the side openings 56 of the long board 30. He then connects the lower straps 37 to the shoulder straps 36, possibly wrapping them around the hands to immobilize the patient. Lastly, the auxiliary strap 57 restrains the patient's feet upon the board 30.

Accordingly, what is claimed is:

1. A set of straps for use with a torso board having first and second openings, said second opening being near the hip on one side of an average person when said first opening is near the shoulder on the other said of said average person, said set of straps comprising:

(A) a first elongated flexible strap having first attaching means for adhering one end of said first strap to said board at said first opening and for preventing the other end of said first strap from moving beyond a predetermined maximum distance away from said first opening when said one end is adhered to said board;

(B) a second elongated flexible strap having second attaching means for adhering one end of said second strap to said board at said second opening and for preventing the other end of said second strap from moving beyond a predetermined maximum distance from said second opening when said one end of said second strap is adhered to said board at said second opening, said one end of said second strap including a section of loops connected to a section of hooks on the side of said section of hooks opposite the side with said hooks and at a point intermediate to longitudinal ends of said sections of hooks, said section of hooks in either longitudinal side of said point being free to move out of contact with said section of loops; and (C) connecting means coupled to said first and second straps and having first and second portions, said first portion forming part of said first strap and a second portion forming part of said second strap, for adjoining said other ends of said first and second straps together sufficiently tightly to prevent relative motion between said other ends when said first and second straps experience forces pulling them away from each other, said connecting means being capable of existing in a plurality of different connecting configurations of said first portion relative to said second portion, each of said connecting configurations adjoining said other ends together, said different connecting configurations differing from one another in total maximum distances along said adhered straps from said first opening to said second opening, said first attaching means being for adhering said one end of said first strap to said first opening without said first strap necessarily contacting any part of said second strap, said second attaching means being for adhering said one end of said second strap to said second opening without said second strap necessarily contacting any part of said first strap, and said second attaching means being capable of existing in a plurality of different attaching configurations, said second attaching means in each of said attaching configurations adhering said one end of said second strap to said board at said second opening, said attaching configurations differing from one another by establishing different predetermined maximum distances of said other end of said second strap from said second opening.

2. The set of straps of claim 1 wherein said first attaching means is capable of existing in a plurality of different configurations, said first attaching means in each of said different configurations of said first attaching means affixing said first strap to said board at said first opening, said different configurations differing from one another by establishing different predetermined maximum distances between said other end of said first strap and said first opening.

3. The set of straps of claim 2 wherein said connecting means includes tension maintaining means for, while said connecting means undergoes a change between said configurations and a particular one of said other ends of said first and second straps is manually held, maintaining contact between said first and second portions of said connecting means and maintaining tension on said first and second straps in a direction away from said first and second openings, respectively.

4. The set of straps of claim 3 wherein said connecting means includes a section of hooks and a section of loops, said section of hooks being engageable with said section of loops, said section of hooks being engaged with said section of loops when said first and said second portions of said connecting means are engaged with each other.

5. The set of straps of claim 4 wherein said one end of said first strap and said one of said second strap each has a section of hooks and a section of loops, said section of hooks being engageable with said section of loops after said one ends have passed through said first and second openings, respectively, in said board, but with one of said sections of loops and hooks, for each of said first and second straps, having passed through said opening in said board and the other of said sections of loops and hooks, for each of said first and second straps, not having passed through said opening.

6. The set of straps of claim 4 wherein said first portion of said connecting means includes a loop attached to one of said first and second straps, and said second portion includes said section of hooks and a section of loops connected to the other of said first and second straps, at least part of said section of hooks, after passing through said loop being engageable with at least part of said section of loops on the other side of said loop.

7. The set of straps of claim 6 wherein said loop is formed from metal and attached to said first strap and said section of loops and said section of hooks form part of said second strap.

8. The set of straps of claim 7 wherein said other end of said second strap includes a section of loops connected to a section of hooks on the side of said section of hooks opposite the side with said hooks and at a point intermediate to longitudinal ends of said section of hooks, said section of hooks on either longitudinal side of said point being free to move out of contact with said section of loops.

9. The set of straps of claim 4 wherein said other end of said second strap includes a section of loops connected to a section of hooks on the side of said section of hooks opposite the side with said hooks and at a point intermediate to longitudinal ends of said section of hooks, said section of hooks on either longitudinal said of said point being free to move out of contact with said section of loops.

10. A method of restraining a person upon a torso board having an area at least as large as the torso of an average sized person and first, second, third, and fourth openings, said second opening being near the hip on a first side of said average person when said first opening is near the shoulder on the second side of said average person, and, with said second opening being near said hip on said first side and said first opening is near said shoulder or said second side, said third and fourth openings are respectively near the shoulder and the hip on the first and second side, said method comprising:
   (A) attaching one end of a first elongated flexible strap to said board at said first opening in a manner to prevent the other end of said first strap from moving beyond a predetermined distance away from said first opening;
   (B) without necessarily contacting said first strap, attaching one end of a second elongated flexible strap in any one of a plurality of different attaching configurations to said board at said second location in a manner to prevent the other end of said second strap from moving beyong a predetermined distance from said second opening, each of said attaching configurations differing from one another by establishing different predetermined maximum distances of said other end of said second strap from said second opening; and
   (C) with connecting means coupled to said first and second straps and having first and second portions, said first portion forming part of said first strap and said second portion forming part of said second strap, connecting together the other ends of said first and second straps in any one of a plurality of different connecting configurations sufficiently tightly to prevent relative motion between said other ends when said first and second straps experience forces pulling them away from each other, each of said different connecting configurations differing from one another in total maximum distances along said attached straps from said first opening to said second opening.

11. The method of claim 10 wherein the step of attaching said one end of said first strap is accomplished by passing said one end through said first opening and engaging a section of hooks on said first strap with a section of loops on said first strap, one of said sections of loops and hooks on said first strap having passed through said first opening and the other of said sections of loops and hooks on said first strap not having passed through said first opening; and the step of attaching said one end of said second strap is accomplished by passing said one end of said second strap through said second opening and engaging a section of hooks on said second strap with a section of loops on said second strap, one of said sections of hooks and loops on said second strap having passed through said second opening and the other of said sections of loops and hooks on said second strap not having passed through said second opening.

12. The method of claim 11 wherein the step of connecting said other ends of said first and second straps is accomplished by passing said other end of one of said first and second straps through a metal loop connected to said other end of the other of said first and second straps and engaging a section of hooks on said other end of said one of said first and second straps with a section of loops on said one of said first and second straps, one of said sections of loops and hooks on said other end of said one of said first and second strap having passed through said metal loop and the other of said section of loops and hooks on said other end of said one of said first and second straps not having passed through said metal loop.

13. An appliance for moving an injured person comprising:
 (1) a torso board having an area at least as large as the torso of an average sized person and first, second, third, and fourth openings, said second opening being near the hip on a first side of said average sized person when said first opening is near the shoulder on the second side of said average sized person, and, with said second opening being near said hip on said first side and said first opening is near said shoulder on said second side, said third and fourth openings are respectively near the shoulder and the hip on the first and second sides, respectively, of said average sized person; and
 (2) a set of straps including:
  (A) a first elongated flexible strap having first attaching means for adhering one end of said first strap to said board at said first opening and for preventing the other end of said first strap from moving beyond a predetermined maximum distance away from said first opening when said one end is adhered to said board;
  (B) a second elongated flexible strap having second attaching means for adhering one end of said second strap to said board at said second opening and for preventing the other end of said second strap from moving beyond a predetermined maximum distance from said second opening when said one end of said second strap is adhered to said board at said second opening; and
  (C) connecting means coupled to said first and second straps and having first and second portions, said first portion forming part of said first strap and a second portion forming part of said second strap, for adjoining said other ends of said first and second straps together sufficiently tightly to prevent relative motion between said other ends when said first and second straps experience forces pulling them away from each other, said connecting means being capable of existing in a plurality of different connecting configurations of said first portions relations to said second portions, each of said connecting configurations adjoining said other ends together, said different connecting configurations differing from one another in total maximum distances along said adhered straps from said first opening to said second opening,
 said first attaching means being for adhering said one end of said first strap to said first opening without said first strap necessarily contacting any part of said second strap, said second attaching means being for adhering said one end of said second strap to said second opening without said second strap necessarily contacting any part of said first strap, and said second attaching means being capable of existing in a plurality of different attaching configurations, said second attaching means in each of said attaching configurations adhering said one end of said second strap to said board at said second opening, said attaching configurations differing from one another by establishing different predetermined maximum distances of said other end of said second strap from said second opening.

* * * * *